(12) United States Patent
Lewis et al.

(10) Patent No.: US 8,394,132 B2
(45) Date of Patent: Mar. 12, 2013

(54) ORTHOPEDIC COMPRESSION SCREW

(75) Inventors: Derek S. Lewis, Copley, OH (US); Deepa Mani, Stow, OH (US); David B. Kay, Akron, OH (US); Amanda Martin, Norton, OH (US)

(73) Assignee: Orthohelix Surgical Designs, Inc., Medina, OH (US)

( * ) Notice: Subject to any disclaimer, the term of this patent is extended or adjusted under 35 U.S.C. 154(b) by 639 days.

(21) Appl. No.: 12/283,777

(22) Filed: Sep. 16, 2008

(65) Prior Publication Data

US 2010/0069970 A1 Mar. 18, 2010

(51) Int. Cl.
*A61B 17/58* (2006.01)

(52) U.S. Cl. ........ 606/301; 606/304; 606/305; 606/309; 606/311; 606/319; 606/321

(58) Field of Classification Search ............... 606/300, 606/301, 304, 305, 319; 411/396, 399, 401
See application file for complete search history.

(56) References Cited

U.S. PATENT DOCUMENTS

| | | | | |
|---|---|---|---|---|
| 298,427 | A | * | 5/1884 | Stone ........................... 411/399 |
| 465,101 | A | * | 12/1891 | Richards ........................ 411/399 |
| 1,151,861 | A | * | 8/1915 | Brumback .................... 411/399 |
| 1,175,665 | A | * | 3/1916 | Sweet ........................... 411/403 |
| 2,347,360 | A | * | 4/1944 | Muenchinger ................. 411/423 |
| 3,552,389 | A | | 1/1971 | Allgower et al. |
| 3,554,193 | A | | 1/1971 | Konstantinou |
| 3,903,784 | A | * | 9/1975 | Dekker ........................... 411/399 |
| RE28,841 | E | | 6/1976 | Allgower et al. |
| 4,219,015 | A | | 8/1980 | Steinemann |
| 4,408,601 | A | | 10/1983 | Wenk |
| RE31,628 | E | | 7/1984 | Allgower et al. |
| 4,513,744 | A | | 4/1985 | Klaue |
| 4,537,185 | A | | 8/1985 | Stednitz |
| 4,708,132 | A | | 11/1987 | Silvestrini |
| 4,716,893 | A | | 1/1988 | Fischer et al. |
| 4,760,843 | A | | 8/1988 | Fischer et al. |
| 5,011,274 | A | * | 4/1991 | Wagner .......................... 351/121 |

(Continued)

FOREIGN PATENT DOCUMENTS

| | | |
|---|---|---|
| DE | 3434807 | 12/1984 |
| DE | 3538238 | 9/1986 |

(Continued)

*Primary Examiner* — Kevin T Truong
*Assistant Examiner* — Zade Coley
(74) *Attorney, Agent, or Firm* — Hudak, Shunk & Farine Co. LPA

(57) ABSTRACT

A cannulated compression screw is used as an orthopedic implant and has a threaded distal end with an insertion tip that includes at least one and preferably two, three or four flutes to allow the screw to be self-tapping. Optionally, the screw also includes one or more reverse cutting flutes proximal to the insertion tip. The distal threads are cancellous threads having a generally constant minor diameter and a generally constant major diameter and a generally constant thread pitch. An intermediate portion of the screw is non-threaded and the proximal end includes a compression wedge or taper that has at least one, and preferably two to five flutes that terminate before the top of the screw. The proximal end further includes a radiused bevel to the terminal surface that includes a hexagonal torque driving recess. The diameter of the non-threaded shaft section is constant distal from the compression wedge to the distal tip where it defines the minor diameter of the threaded portion. The screw optionally includes a tapered insertion tip.

3 Claims, 1 Drawing Sheet

U.S. PATENT DOCUMENTS

| | | | |
|---|---|---|---|
| 5,019,080 A | 5/1991 | Hemer | |
| 5,122,133 A * | 6/1992 | Evans | 606/301 |
| 5,129,901 A * | 7/1992 | Decoste | 606/65 |
| 5,169,400 A | 12/1992 | Muhling et al. | |
| 5,318,570 A * | 6/1994 | Hood et al. | 606/99 |
| 5,334,204 A * | 8/1994 | Clewett et al. | 606/312 |
| 5,364,400 A | 11/1994 | Rego, Jr. et al. | |
| 5,403,136 A | 4/1995 | Mathys | |
| 5,516,248 A * | 5/1996 | DeHaitre | 411/387.2 |
| 5,562,673 A * | 10/1996 | Koblish et al. | 606/80 |
| 5,683,217 A * | 11/1997 | Walther et al. | 411/399 |
| 5,743,914 A * | 4/1998 | Skiba | 606/304 |
| 5,797,914 A | 8/1998 | Leibinger | |
| 5,816,812 A * | 10/1998 | Kownacki et al. | 433/174 |
| 5,842,865 A * | 12/1998 | Bassett et al. | 433/174 |
| 5,925,048 A | 7/1999 | Ahmad et al. | |
| 5,954,722 A | 9/1999 | Bono | |
| 6,030,162 A * | 2/2000 | Huebner | 411/413 |
| 6,068,632 A * | 5/2000 | Carchidi et al. | 606/79 |
| 6,235,033 B1 | 5/2001 | Brace et al. | |
| 6,290,444 B1 * | 9/2001 | Dicke | 411/399 |
| D449,692 S | 10/2001 | Michelson | |
| 6,306,140 B1 * | 10/2001 | Siddiqui | 606/315 |
| 6,322,562 B1 | 11/2001 | Wolter | |
| 6,355,043 B1 | 3/2002 | Adam | |
| 6,402,757 B1 * | 6/2002 | Moore et al. | 606/80 |
| 6,565,573 B1 | 5/2003 | Ferrante et al. | |
| 6,575,975 B2 | 6/2003 | Brace et al. | |
| 6,620,195 B2 | 9/2003 | Goble et al. | |
| 6,629,977 B1 | 10/2003 | Wolf | |
| 6,635,059 B2 | 10/2003 | Randall et al. | |
| 6,676,353 B1 * | 1/2004 | Haytayan | 411/442 |
| 6,730,092 B2 | 5/2004 | Songer | |
| 6,733,502 B2 | 5/2004 | Altarac et al. | |
| 6,875,216 B2 | 4/2005 | Wolf | |
| 6,890,334 B2 | 5/2005 | Brace et al. | |
| 7,037,309 B2 * | 5/2006 | Weil et al. | 606/304 |
| 7,325,470 B2 * | 2/2008 | Kay et al. | 81/451 |
| 7,708,738 B2 * | 5/2010 | Fourcault et al. | 606/67 |
| 7,731,738 B2 * | 6/2010 | Jackson et al. | 606/304 |
| 7,799,061 B2 * | 9/2010 | Kay et al. | 606/283 |
| 7,955,364 B2 * | 6/2011 | Ziolo et al. | 606/308 |
| 2003/0028193 A1 | 2/2003 | Weil et al. | |
| 2003/0045881 A1 | 3/2003 | Barouk et al. | |
| 2003/0074002 A1 | 4/2003 | West, Jr. | |
| 2003/0125744 A1 | 7/2003 | Contiliano et al. | |
| 2003/0125749 A1 | 7/2003 | Yuan et al. | |
| 2003/0153919 A1 | 8/2003 | Harris | |
| 2003/0158555 A1 | 8/2003 | Sanders et al. | |
| 2003/0187447 A1 | 10/2003 | Ferrante et al. | |
| 2003/0199878 A1 | 10/2003 | Pohjonen et al. | |
| 2004/0006345 A1 | 1/2004 | Vlahos et al. | |
| 2004/0030336 A1 | 2/2004 | Khanna | |
| 2004/0068319 A1 | 4/2004 | Cordaro | |
| 2005/0085913 A1 | 4/2005 | Fraser et al. | |
| 2005/0096657 A1 | 5/2005 | Autericque et al. | |
| 2006/0173462 A1 * | 8/2006 | Kay et al. | 606/73 |
| 2006/0200128 A1 * | 9/2006 | Mueller | 606/61 |
| 2006/0200151 A1 | 9/2006 | Ducharme et al. | |
| 2007/0212915 A1 * | 9/2007 | Strnad et al. | 439/248 |
| 2007/0239163 A1 * | 10/2007 | Strnad et al. | 606/72 |
| 2008/0124187 A1 * | 5/2008 | Haytayan | 411/387.1 |
| 2008/0132958 A1 | 6/2008 | Pech et al. | |
| 2008/0193234 A1 * | 8/2008 | Davancens et al. | 408/1 R |
| 2008/0234763 A1 * | 9/2008 | Patterson et al. | 606/315 |
| 2008/0243189 A1 * | 10/2008 | Purcell et al. | 606/264 |
| 2008/0249574 A1 * | 10/2008 | McCombs et al. | 606/301 |
| 2009/0118771 A1 * | 5/2009 | Gonzalez-Hernandez | 606/286 |
| 2009/0248087 A1 * | 10/2009 | Lewis et al. | 606/301 |
| 2010/0042162 A1 * | 2/2010 | Edie et al. | 606/301 |

FOREIGN PATENT DOCUMENTS

| | | |
|---|---|---|
| DE | 3601865 | 1/1987 |
| EP | GB 2 132 487 | 7/1984 |
| EP | 0 172 130 | 2/1986 |
| EP | 0 299 160 | 1/1989 |

* cited by examiner

ORTHOPEDIC COMPRESSION SCREW

FIELD OF THE INVENTION

The invention relates to a compression screw for use as an orthopedic implant in particular for stand alone applications in small bones. The screw has a tapered proximal portion with at least one cutting flute which terminates prior to the proximal end of the taper (i.e. prior to the widest diameter) so as to form a respective lip which acts as a stop to the axial advancement of the screw into bone. A threadless constant diameter intermediate segment separates the proximal portion from the cancellous threads and fluted distal insertion tip.

BACKGROUND OF THE INVENTION

The use of implants in the field of orthopedic surgery has a relatively recent history, even including the use of screws, which can be used to hold plates or rods in position, or to hold bones or bone fragments in place to facilitate fusion between bone surfaces. Achieving repair across a fracture, or fusion between two otherwise unrelated bone segments through the use of a stand-alone screw, is often furthered by causing compression of the segments at the cortical surfaces. The prior art has recognized the use of screws that generate this kind of compression, and includes compression screws that are self-tapping, self-drilling and self countersinking. The present screw is designed to maximize the ease of insertion and the compression generated, in particular to suit the needs of small bone surgeons. This area includes bones distal to the elbow or knee that are smaller more delicate bones than the long bones, and further are bones that function in conjunction with less, and more delicate, soft tissue in order to achieve movements with greater finesse than the gross apendicular movement. There is often little bone for purchase, and even less muscle tissue to provide a buffer for protruding tips. Consequently, it is imperative in the small bone context that implants are designed to maximize the desired result with a minimum of volume. The present invention is designed to provide both a maximum of compression along the longitudinal axis of the screw and to provide for ease of insertion by lessening the need for an additional drilling step.

The present invention can be used for fixation or repair following trauma, for example of the scaphoid bone, or for correction of a developed condition such as bunion or congenital defect like flat feet. Thus, the present invention relates generally to a class of screw known as a "compression screw", and more specifically to those classed as "headless compression screws" which generally refer in the orthopedic arts to screws which are countersunk so that they that do not project beyond the surface of the bone in use. The present invention has a threaded distal end, which is preferably self-tapping and a proximal end, which has a compression taper or wedge. This area has an increasing diameter toward the distal end, such as is provided, for example, by a frusto-conical or domed shape to the maximum diameter area of the wedge. Beyond the maximum, the proximal portion includes a bevel or rounded edge that terminates in a flat proximal terminal surface that includes a torque driving recess, This proximal taper area has one or more, and preferably two to four, equally spaced cutting flutes, which also end at or below the rounded edge of the wedge. The flute or flutes do not extend through to the proximal terminal surface of the screw, and in fact end substantially before the end, meaning that a circumferential fillet or lip is formed at the top of each cutting flute by that portion of the taper which is proximally distant to the flute. Preferably this feature provides a plurality of lips that act as a stop portion located proximally at or below about the widest portion of the compression wedge. Thus, the proximal compression taper is self-drilling to the bone cortex, but will act to generate compression when the distal side of the lip engages the cortical bone that forms the top of the screw hole. Thus, in one specialized sense this stop portion can be considered to be a "head" in so far as it is not self-countersinking and in that it increases the longitudinal compression generated at the proximal portion of the screw, in particular because of the composition of bone at this surface. It is not intended to sit proud to the bone surface nor to be countersunk, but rather to sit flush with it unless the bone is subjected to a counterboring step prior to implantation. This design helps to provide optimal compression by causing the screw to impact the hard cortical portion of the bone and to thus drive the bone toward the distal end of the screw. Thus, the product is considered to be "self-drilling" but not "self-countersinking. This is an aspect of the invention that distinguishes it from the prior art "headless compression screws".

BRIEF DESCRIPTION OF THE DRAWINGS

The invention will be better understood and other features and advantages will become apparent by reading the detailed description of the invention, taken together with the drawings, wherein.

DETAILED DESCRIPTION OF THE DRAWINGS

Figure 1:
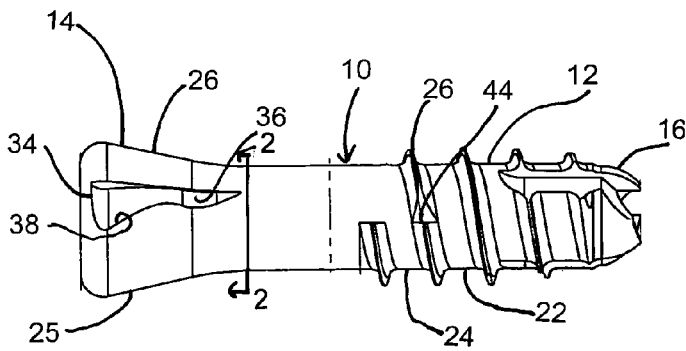
FIG. 1 is a side view of a compression screw in accordance with the present invention.
Figure 2:
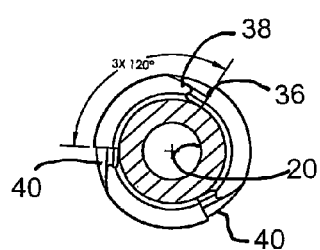
FIG. 2 is a cross-section of the screw taken along line 2-2.
Figure 3:
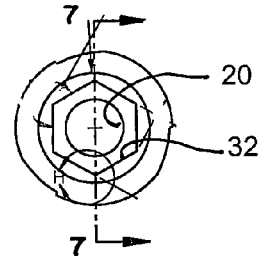
FIG. 3 is a top view of the screw.
Figure 4:
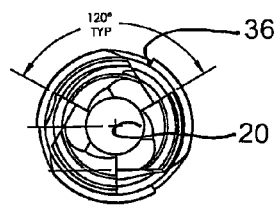
FIG. 4 is an end view of the screw.
Figure 5:
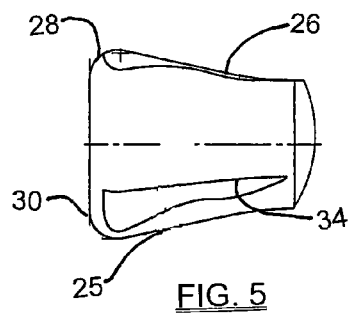
FIG. 5 is detail of the proximal portion of the screw.
Figure 6:
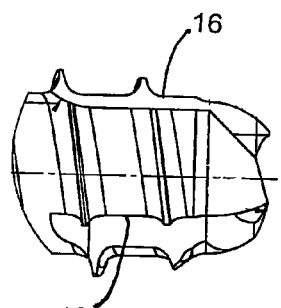
FIG. 6 is a detail of the insertion tip of the screw.
Figure 7:
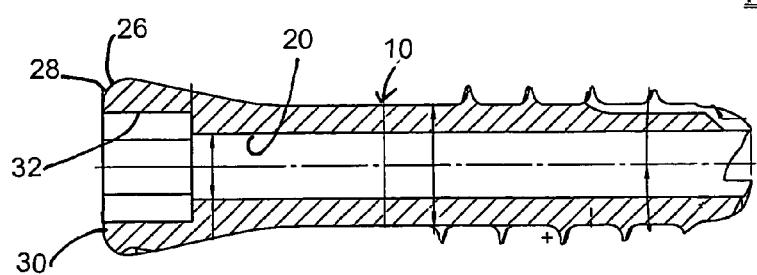
FIG. 7 is a cross-section of the screw taken along line 7-7.

FIGS. 1-7 show a compression screw 10 in accordance with the present invention. The screw 10 includes a threaded distal portion 12 and a proximal compression portion 14. The distal portion of the screw 10 includes an insertion tip 16 that is preferably self-starting and self-tapping. The term "distal" is used herein to mean the end that would be farthest along the longitudinal axis from the area that is driven by the screw-driver, and "proximal" is used to mean the opposite end of the screw, i.e. the torque driving portion. Preferably, the distal terminus of the insertion tip is designed to avoid sharp edges that might project beyond the edge of the bone and cause irritation to the surrounding soft tissue. This feature is shown as a taper, but could include a rounded shape instead. The insertion tip 16 has at least one, and preferably a plurality of cutting flutes 18 or grooves that form sharp cutting surfaces at the terminus of the screw. Optimally, there are from 2 to 5, and more preferably about 3 equally spaced flutes with a first surface that defines a plane that dissects the longitudinal axis of the screw and a second surface that defines a plane at about a 90° angle to the first flute surface plane. The first surface is cut at a 45° angle to a central bore 20 that forms a cannula in the screw.

Extending proximally from the insertion tip 16, the screw 10 includes a threaded portion 22 having a constant minor diameter 24 and a constant major diameter 26 (i.e. to form a section having a constant thread depth). The insertion tip also includes a thread run out so that this portion of the screw does not have a constant thread depth and the minor diameter of the insertion tip includes a slight taper, i.e. of from about 2° to about 6°, preferably of from about 3° to about 5°, and more preferably between about 4° and about 5°. Further preferably, the thread pitch is constant along the length of the threaded section 22. The thread is a cancellous thread. A threadless intermediate section 24 joins the proximal portion 25 with the threaded portion of the screw and the intermediate section has the same diameter as the minor diameter of the threaded portion 22 of the screw. The intermediate portion is from about one third to about three times the longitudinal length of the threaded portion, and preferably from about one third to about the length of the threaded portion from the tip to the proximal beginning of the thread.

The screw 10 of the present invention includes a partial or full cannula 20 along its longitudinal axis. While the screw is shown as including a through bore in the drawings, the bore can project only partially toward the distal end of the screw, or can be absent.

The proximal portion 25 of the screw includes a compression wedge defined by a side wall 26 and shown as a portion of a cone that increases in diameter at an angle of from about 5° to about 20°, and preferably from about 10° to about 15°, and more preferably between about 12° and about 13°, along the longitudinal axis in the direction of the proximal end from the minor diameter of the threaded area to a maximum diameter. The compression wedge can instead be formed as a portion of a sphere, an egg shape, a square, or a compound shape. In the event that the wedge forms some shape other than a right angle cone, the plane defining the angle of the side wall to the longitudinal axis can be determined from the cross section of the screw by finding a line that best approximates the thrust of the compression head. Proximal to the maximum diameter, the proximal portion 25 has a bevel, rounded edge or shoulder 28 that transitions into the terminal surface 30. Thus, the wedge forms a shape that may be be linear or curved in cross section but which terminates in an area of maximum diameter and is radiused into the terminal end which includes the torque driving recess 32. The length of the compression wedge along the longitudinal axis is from about one fourth to about three times the longitudinal length of the intermediate portion, and preferably from about one fourth to about twice the length, and most preferably from about one half to about the same length, depending on the screw length. This section of the wedge also includes at least one cutting flute 34, and preferably from about two to about five, and most preferably either three or four flutes that are equally spaced and spaced apart from or "clocked" apart from the cutting flutes on the insertion tip. These flutes include a first flute surface 36 that defines a plane that intersects the longitudinal axis of the screw, and at a 90° angle to that first surface plane has a second surface 38 that runs parallel to the longitudinal axis of the screw. The second surface preferably defines a compound curve that has a less aggressive cutting area so as to provide for more screw material radially opposite the place where the torque driving recess joins the cannula. This helps to inhibit the screw from shearing at that point during insertion. The second surface ends at a radial angle of about 30° to the first edge. Each of the cutting flutes terminate at the same axial distance and before the shoulder of the tapered portion. Thus, these flutes define a small circumferential lip or fillet 40 that helps to define the bottom of the shoulder so as to define the suggestion of a "head" which is joined to the area of maximum diameter of the taper. Optionally, the threaded portion 22 of the screw includes at least one and preferably from about 1 to about 4 reverse cutting flutes 44 which form a first cutting edge in the thread in the opposite direction of the first surface of the proximal and distal cutting flutes.

The screw head has a relatively flat proximal surface 38 having shoulders 28 formed by radiused transitions into the tapered area of the side wall 26 of the proximal portion 25. The proximal surface includes a torque driving recess 32 which can be a hexagon, other appropriate torque driving shape, such as a hexalobe style recess.

The screw can be made from an appropriate biocompatible material having appropriate strength characteristics including surgical grade stainless steel or titanium or absorptive materials.

While in accordance with the patent statutes the best mode and preferred embodiment have been set forth, the scope of the invention is not limited thereto, but rather by the scope of the attached claims.

What is claimed is:

1. An orthopedic screw for implantation into bone comprising:
    a proximal end and a distal end and a longitudinal axis extending therebetween;
    a cannula extending through the screw along the longitudinal axis;
    a distal portion having an insertion tip which includes from 3 to 5 grooves equally radially spaced and extending in the direction of the longitudinal axis which each form a distal cutting flute that cuts as the screw is being screwed into the bone;
    a threaded portion adjoining the distal portion having a substantially constant minor diameter and a substantially constant major diameter and a substantially constant thread pitch, said thread being a cancellous thread, said threaded portion including at least one reverse flute which cuts as the screw is being screwed out of the bone;
    an intermediate cylindrical portion adjoining the threaded portion which is substantially free from the cancellous thread of the threaded portion and having a diameter which is substantially the same diameter as the minor diameter of the threaded portion, and which is from about one half to about twice the longitudinal length of the threaded portion; and
    a proximal non-threaded wedge portion adjoining the intermediate cylindrical portion and which has a diameter that constantly increases from the diameter of the intermediate portion to a maximum diameter which is larger than the major diameter of the threaded portion so as to form a cone that defines a side wall which defines a plane that has an angle with the longitudinal axis of from about 11° to 13° and the side wall including from 3 to 5 radially equally spaced proximal cutting flutes that have a first surface which defines a plane that transects the longitudinal axis and a second surface that forms an angle of from about 60° to about 120° to the first surface and a radial angle of about 20° to about 40° to the plane of the first surface, the proximal cutting flutes cutting when the screw is being screwed into the bone and being radially offset from the distal cutting flutes, the side wall proximally terminating in a rounded shoulder portion that joins a proximal end terminal surface, and the proximal cutting flutes each terminating in the longitudinal direction distal to the rounded shoulder portion to form a lip that is open toward a distal end of the screw, the proximal gad terminal surface including a torque driving recess that extends distally along the longitudinal axis of the screw and which terminates at a first distance from the proximal end of the screw whereby the lip is located at or distal to a widest portion of the proximal non-threaded wedge portion and comprises a circumferential fillet which acts as a stop portion in use, and the second surface of the proximal cutting flutes each defining a compound curve so that the material of the screw is augmented in the proximal portion of the screw at the first distance from the proximal end of the screw.

2. An orthopedic screw as set forth in claim 1 in which the torque driving recess is a hexagon or a hexalobe shape.

3. An orthopedic screw as set forth in claim 1 wherein the insertion tip includes a taper.

* * * * *